US00PP30508P2

(12) United States Plant Patent
Tsukahara

(10) Patent No.: US PP30,508 P2
(45) Date of Patent: May 14, 2019

(54) COLEUS PLANT NAMED 'SAKCOL023'

(50) Latin Name: ***Solenostemon* sp.**
Varietal Denomination: SAKCOL023

(71) Applicant: Sakata Seed Corporation, Tsuzuki-Ku, Yokohama (JP)

(72) Inventor: Jun Tsukahara, Kakegawa Shizuoka (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 15/732,581

(22) Filed: Nov. 29, 2017

(51) Int. Cl.
*A01H 5/12* (2018.01)
*A01H 5/02* (2018.01)

(52) U.S. Cl.
USPC ..... Plt./469

(58) Field of Classification Search
USPC ..... Plt./373, 469
CPC ..... A01H 5/12
See application file for complete search history.

*Primary Examiner* — Keith O. Robinson
(74) *Attorney, Agent, or Firm* — Bethany Reid Roahrig; Cochran Freud & Young LLC

(57) ABSTRACT

A coleus plant particularly distinguished by a multicolored leaf pattern of bright rose foliage with dark burgundy blotches and venation, and green margins, with a mounding plant habit and small leaves, is disclosed.

1 Drawing Sheet

Genus and species: *Solenostemon* sp.
Variety denomination: 'SAKCOL023'.

BACKGROUND OF THE NEW PLANT

The present invention comprises a new and distinct variety of coleus, botanically known as *Solenostemon* sp., and hereinafter referred to by the variety name 'SAKCOL023'.

'SAKCOL023' originated from the open pollination of 8 unpatented proprietary lines crossed pollinated in October 2014 in Kakegawa, Japan. The breeder put breeding materials '14P-202', '14P-203', '14P-205', '14P-210', '14P-211', '14P-212', '14F-19', and '14F-20-2' in a cage. Bees then crossed them at random. The breeder harvested 1,200 seeds from '14P-211'. These seeds were composed of hybrid seeds and self-pollinated seeds.

The seeds obtained from the '14P-211' plant were sown and a single plant selection designated 'L2015-CO258' was selected for its multicolored leaf pattern with a bright rose foliage with dark burgundy blotches and venation, and green margins with mounding plant habit with small leaves. The breeder confirmed that 'L2015-CO258' was fixed and stable. 'L2015-CO258' was subsequently named 'SAKCOL023'.

The new plant was first asexually propagated from October 2015 to April 2016 in Japan and has been asexually reproduced by vegetative cuttings for almost three years in Japan. The present invention has been found to retain its distinctive characteristics through successive asexual propagations by vegetative cuttings.

'SAKCOL023' has not been made publicly available or sold more than one year prior to the filing date of this application.

SUMMARY OF THE NEW PLANT

The following are the most outstanding and distinguishing characteristics of the new variety when grown under normal horticultural practices in Salinas, Calif.

1. Small leaves; and
2. Bright rose foliage with dark burgundy blotches and venation and green margins.

DESCRIPTION OF THE PHOTOGRAPHS

This new coleus plant is illustrated by the accompanying photograph which shows the overall plant habit and foliage of a plant aged 3 months old. The colors are as true as can be reasonably obtained by conventional photographic procedures.

DESCRIPTION OF THE NEW VARIETY

The following detailed descriptions set forth the distinctive characteristics of 'SAKCOL023'. The data which defines these characteristics were collected from plants grown three months from transplant into 4-inch pots from rooted cuttings in Salinas, Calif., under greenhouse conditions. Color references are to The Royal Horticultural Society Colour Chart, 4$^{th}$ edition. Anatomic labels are from *The Cambridge Illustrated Glossary of Botanical Terms*, by M. Hickey and C. King, Cambridge University Press.

Classification:
*Family*.—Lamiaceae.
*Botanical name*.—*Solenostemon* sp.
*Common name*.—Coleus.
*Denomination*.—'SAKCOL023'.

Plant:
*Type*.—Annual.
*Habit*.—Mounding.
*Form*.—Compact and dense, 5 main branches.
*Height*.—23.5 cm.
*Spread*.—45.0 cm.
*Propagation type*.—Vegetative cuttings.

Environmental conditions for plant growth: The terminal 1.0 to 1.5 inches of an actively growing stem was excised. The vegetative cuttings were propagated for five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24 degrees C.

Lateral branches:

*Length.*—18.5 cm to 20.0 cm.
*Diameter.*—6.0 cm to 9.0 cm.
*Internode length.*—2.5 cm to 3.0 cm.
*Strength.*—Branches separate easily.
*Aspect.*—Long, trailing to semi-trailing.
*Shape in cross-section.*—Circular.
*Texture.*—Dull, very slight pubescent.
*Pubescence color.*—RHS N155A (White).
*Branch color.*—RHS 146C (Yellow-Green) with pronounced line of RHS 59A (Red-Purple) at nodes.
*Stem color.*—Closest to RHS 1D (Green-Yellow), Very distinct pattern with the 1$^{st}$ to 2nd internode being closest to but darker than RHS 187A (Greyed-Purple) on the interior with a transparent layer of RHS 146C (Yellow-Green) over creating a greyed mixture of the two. Also a pronounced line of RHS 59A (Red-Purple) at nodes.
*Flowering branch.*—Present, very slight pubescence.

Leaves:

*Arrangement.*—Opposite.
*Length.*—5.8 cm.
*Width.*—3.5 cm.
*Broadest part of the leaf blade.*—Middle.
*Shape.*—Cordate.
*Apex.*—Lanceolate.
*Base.*—Cordate.
*Margin.*—Very pronounced crenation, wavy.
*Texture, upper surface.*—Dull, very slight pubescence.
*Texture, lower surface.*—Glabrous with pronounced venation.
*Venation pattern.*—Reticulate.
*Vein color, upper surface.*—RHS N77A (Purple).
*Vein color, lower surface.*—Closest to RHS 156C (Greyed-White).
*Petiole length.*—1.2 cm.
*Petiole diameter.*—1.5 mm.
*Petiole color.*—Closest to RHS 2D (Yellow).
*Petiole texture.*—Very slight pubescent.
*Variegation.*—Present.
*Leaf color.*—Multicolored, hot pink at the center with blotches of dark maroon increasing towards margin and green at margin. Younger foliage having slightly lighter and brighter coloration. Mature foliage: Upper surface: RHS 61A (Red-Purple) at center with blotches of RHS 200A (Brown) increasing towards margin and RHS 143A (Green) at margin. Lower surface: Closest to but lighter than RHS 147B (Yellow-Green) with blotches of RHS N79B (Purple) intensified around venation and slight RHS 156C (Greyed-White) at base. Young foliage: Upper surface: Closest to but RHS 61A (Red-Purple) with RHS N34A (Orange-Red) towards margin and blotches of RHS 187A (Greyed-Purple) towards margin and RHS 1B (Yellow) and RHS 143A (Green) at margin. Lower surface: Closest to RHS 161D (Greyed-Yellow) with blotches slightly darker than RHS N71A (Red-Purple) at midpoint and RHS 138A (Green) towards margin.

Flowers: Terminal flower stalk observed having multiple buds and forming a cone shape.

*Stalk length.*—4.5 cm.
*Stalk diameter.*—1.8 cm.
*Internode length.*—Approximately 3.0 mm to 4.0 mm.
*Stalk color.*—Closest to RHS 1B (Yellow) with slight RHS N144D (Yellow-Green).

Temperature tolerance: 2 degrees C. to 35 degrees C.

Disease or insect resistance: No disease or insect resistance observed.

COMPARISON WITH PARENTAL LINES AND KNOWN VARIETY

'SAKCOL023' is a new and distinct cultivar of coleus owning to its unique multicolored leaf pattern and mounding plant habit and small leaves. It is distinguished from its parents as described in Table 1 below.

TABLE 1

Comparison with Parental Lines

| | Leaf color | Leaf size |
|---|---|---|
| Parental lines | | |
| '14P-202' | Brown | Extremely small |
| '14P-203' | Rose and green | Extremely small |
| '14P-205' | Brown | Extremely small |
| '14P-210' | Rose and brown | Small |
| '14P-211' | Rose and green | Small |
| '14P-212 | Rose, brown and green | Large |
| '14F-19' | Dark brown and green | Medium |
| '14F-20-2' | Rose, brown and green | Extremely large |
| Comparison | | |
| 'SAKCOL023' | RHS 61A (Red-Purple) at center with blotches of RHS 200A (Brown) increasing towards margin and RHS 143A (Green) at margin | Small Length: 5.8 cm Width: 3.5 cm |

| | Leaf shape | Leaf margin | Plant habit |
|---|---|---|---|
| Parental lines | | | |
| '14P-202' | Orbicular | Crenate | Creeping |
| '14P-203' | Orbicular | Crenate | Creeping |
| '14P-205' | Orbicular | Crenate | Creeping |
| '14P-210' | Ellipse | Serrate | Mounding |
| '14P-211' | Ellipse | Serrate | Mounding |
| '14P-212 | Ovate | Crenate | Erect |
| '14F-19' | Ovate | Crenate | Erect |
| '14F-20-2' | Orbicular | Crenate | Erect |
| Comparison | | | |
| 'SAKCOL023' | Cordate | Very pronounced crenation, wavy | Mounding |

'SAKCOL023' is most similar to the commercial variety PARTY TIME 'Pink Berry', also known as 'SAKCOL018' (U.S. Plant Pat. No. 28,823) however, there are differences as listed in Table 2 below.

TABLE 2

| Comparison with Similar Variety | | |
|---|---|---|
| Characteristic | 'SAKCOL023' | PARTY TIME 'Pink Berry' |
| Leaf color, upper surface | RHS 61A (Red-Purple) at center with blotches of RHS 200A (Brown) increasing towards margin and RHS 143A (Green) at margin | Closest to RHS 59C (Red-Purple )with blotches closest to RHS 200A (Black) with slight RHS 147A (Green) increasing towards margin, and RHS 143A (Yellow-Green) at leaf margin. |
| Leaf color, lower surface | Closest to but lighter than RHS 147B (Yellow-Green) with blotches of RHS N79B (Purple) intensified around venation and slight | Closest to RHS147B (Yellow-Green) with blotches of RHS 59A (Red-Purple) towards mid vein with most mature foliage |

TABLE 2-continued

| Comparison with Similar Variety | | |
|---|---|---|
| Characteristic | 'SAKCOL023' | PARTY TIME 'Pink Berry' |
| | RHS 156C (Greyed-White) at base | having a blotch closest to RHS 27A (Orange) at base |
| Plant growth habit | Compact, Mounding | Compact, Semi-creeping |

I claim:

1. A new and distinct variety of coleus plant named 'SAKCOL023' as illustrated and described herein.

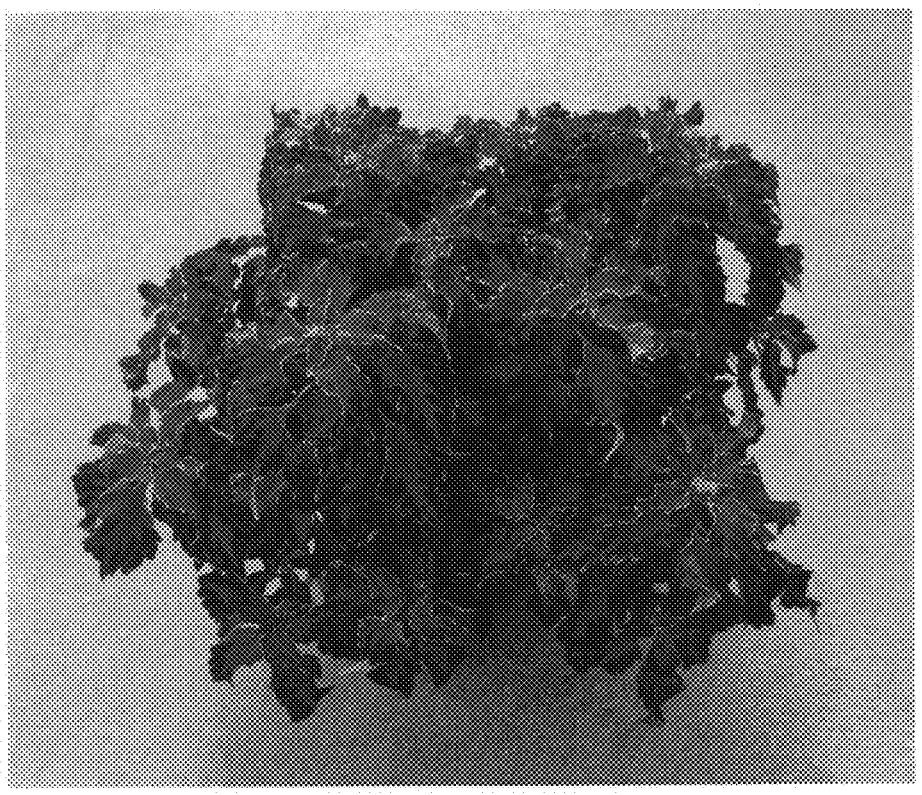

* * * * *